United States Patent
Rogacs et al.

(10) Patent No.: US 10,520,443 B2
(45) Date of Patent: Dec. 31, 2019

(54) FOCAL ADJUSTMENT FOR ANALYTE DETECTION PACKAGE

(71) Applicant: Hewlett-Packard Development Company, L.P., Houston, TX (US)

(72) Inventors: Anita Rogacs, San Diego, CA (US); Viktor Shkolnikov, Palo Alto, CA (US); Ning Ge, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 15/764,240

(22) PCT Filed: Jan. 29, 2016

(86) PCT No.: PCT/US2016/015776
§ 371 (c)(1),
(2) Date: Mar. 28, 2018

(87) PCT Pub. No.: WO2017/131772
PCT Pub. Date: Aug. 3, 2017

(65) Prior Publication Data
US 2018/0275065 A1 Sep. 27, 2018

(51) Int. Cl.
*G01N 21/65* (2006.01)
*G01J 3/44* (2006.01)
*G01N 21/64* (2006.01)

(52) U.S. Cl.
CPC .............. *G01N 21/658* (2013.01); *G01J 3/44* (2013.01); *G01N 21/648* (2013.01)

(58) Field of Classification Search
CPC .... G01N 21/658; G01N 21/648; G01N 21/65; G01J 3/44

USPC ......................................................... 356/301
See application file for complete search history.

(56) References Cited

U.S. PATENT DOCUMENTS

| | | | |
|---|---|---|---|
| 7,450,227 B2 | 11/2008 | Dwight et al. | |
| 7,956,995 B2 | 6/2011 | Suzuki et al. | |
| 8,093,065 B2 | 1/2012 | Poponin | |
| 2005/0226765 A1 | 10/2005 | Bone et al. | |
| 2006/0023209 A1 | 2/2006 | Lee et al. | |
| 2007/0252983 A1 | 11/2007 | Tong et al. | |
| 2012/0013903 A1 | 1/2012 | Kuo et al. | |
| 2012/0170050 A1 | 7/2012 | Savran et al. | |
| 2012/0200851 A1* | 8/2012 | Wu ...................... | G01N 21/658 356/301 |
| 2015/0065390 A1 | 3/2015 | Bratkovski | |

FOREIGN PATENT DOCUMENTS

| | | |
|---|---|---|
| EP | 1766458 A2 | 3/2007 |
| EP | 2386847 A2 | 11/2011 |
| JP | 2010243267 | 10/2010 |
| WO | WO-2004090505 | 10/2004 |

* cited by examiner

*Primary Examiner* — Hina F Ayub
(74) *Attorney, Agent, or Firm* — Dicke Billig & Czaja PLLC

(57) ABSTRACT

An analyte detection system includes an analyte detection package to be presented to a reading device, and a focus mechanism to adjust a focal point of the analyte detection package relative to the reading device, with the analyte detection package including a surface-enhanced luminescence analyte stage, the reading device including optics to receive scattered radiation emitted luminescence from the analyte stage, and the focus mechanism to adjust the focal point relative to the optics.

20 Claims, 7 Drawing Sheets

FOCAL ADJUSTMENT FOR ANALYTE DETECTION PACKAGE

BACKGROUND

Surface-enhanced luminescence techniques, such as surface-enhanced Raman spectroscopy (SERS), may be used to analyze the structure of inorganic materials or complex organic molecules. Surface-enhanced luminescence techniques focus electromagnetic radiation or light onto an analyte, wherein the radiation scattered or re-emitted by the analyte is detected for analysis.

DETAILED DESCRIPTION

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure.

The present disclosure provides a mechanism to adjust a focus of an analyte detection package. The focus mechanism provides for movement or adjustment of a focal point of the analyte detection package relative to a reading device including, more specifically, movement or adjustment of a focal length between an analyte stage of the analyte detection package and optics of the reading device. In this regard, the focal length may be aligned with a focal plane of the optics of the reading device such that the analyte detection package is "in-focus".

Figure 1:
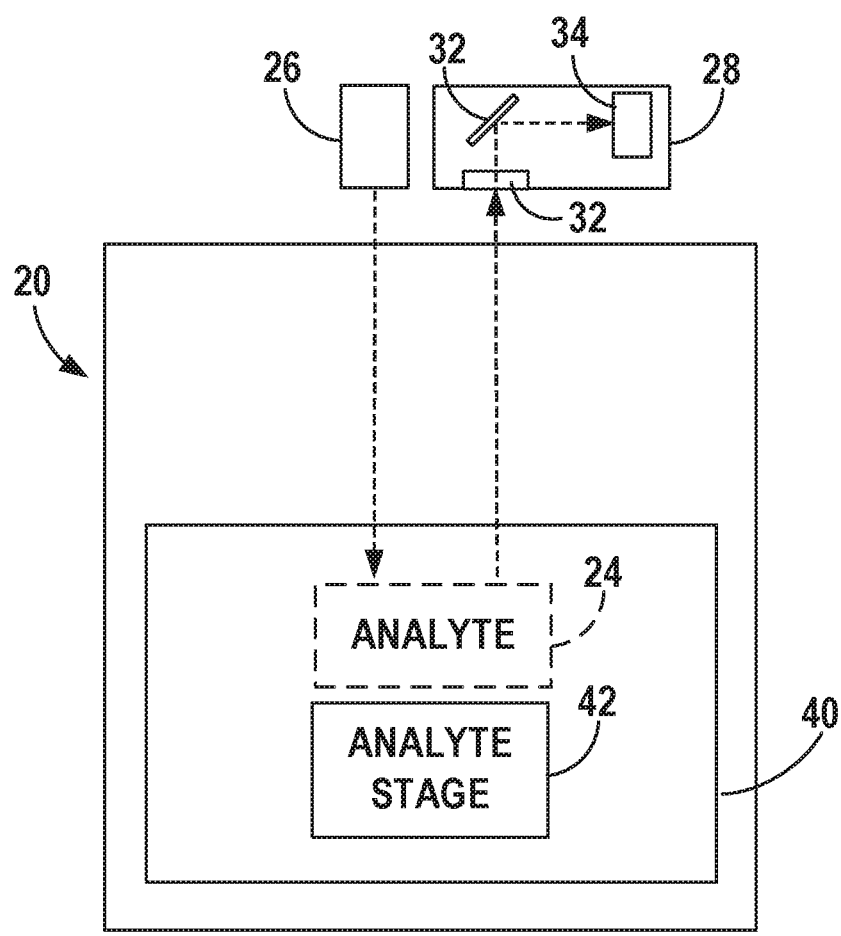
FIG. 1 is a schematic diagram of an example analyte detection package.

FIG. 1 schematically illustrates an example analyte detection package 20. Package 20 comprises a self-contained unit that is to receive and contain an analyte 24 (schematically shown), while radiation from a radiation source 26 (schematically shown) is directed upon or is focused on analyte 24, wherein the radiation scattered or re-emitted by the analyte (i.e., emitted luminescence) is detected by a reading device 28 (schematically shown) and analyzed, for example, to identify the structure of inorganic materials or complex organic molecules. In one implementation, package 20 comprises a chamber 40 and an analyte stage 42, and reading device 28 comprises optics, including optics 32, for directing scattered radiation or emitted luminescence to a detector 34.

Chamber 40 contains stage 42 and comprises an enclosure forming a defined volume for receiving and containing analyte 24. In one implementation, chamber 40 is formed by a substrate and an opposite or overlying housing which cooperate to form chamber 40. In one implementation, walls of chamber 40 have a metal or metal alloy surface, such as a surface of nickel, gold, platinum, palladium, or rhodium, or alloys thereof.

In one implementation, chamber 40 includes a fill opening through which analyte 24 is deposited into chamber 40. In one implementation, the fill opening is closed by a removable seal that may be peeled away, punctured or torn to expose the fill opening. In one implementation, the fill opening is formed by peeling, puncturing or penetrating through a portion of a wall of chamber 40. In one implementation, a portion of chamber 40 is to be torn away or peeled away to form the fill opening. In another implementation, chamber 40 has a portion which is to be punctured. In another implementation, chamber 40 comprises a septum through which a needle is used to deposit analyte 24 into the interior of chamber 40.

In one implementation, analyte stage 42 comprises a surface-enhanced luminescence analyte stage within chamber 40. A surface-enhanced luminescence (SEL) analyte stage includes any structure or particle that interacts with the deposited analyte so as to enhance the intensity of the radiation scattered or reemitted by the analyte. SEL analyte stage 42 enhances the amount of radiation or the number of photons that are scattered or re-emitted by the analyte upon being impinged by radiation from radiation source 26.

In one implementation, analyte stage 42 comprises an SEL structure or a group of SEL structures within chamber 40 upon which or about which analyte 24 contacts or collects. In one implementation, the SEL structures comprise enhanced fluorescence spectroscopy structures or enhanced luminescence spectroscopy structures.

In one implementation, the SEL structures comprise surface-enhanced Raman spectroscopy (SERS) structures. Such structures may include a metal surface or structure, wherein interactions between the analyte and the metal surface cause an increase in the intensity of the Raman-scattered radiation or emitted luminescence. Such metal surfaces may include a roughened metal surface or metal islands. In one implementation, such metal islands comprise columnar structures such as pillars, needles, fingers or wires. In some implementations, the columnar structures may include a metal cap or head upon which analyte 24 may be deposited. In one implementation, the SER structures have a nanometer scale to facilitate nano-enhanced Raman spectroscopy (NERS). Such nano-scale NERS structures may increase, for example, by a factor as high as $10^{16}$, the intensity of radiation scattered or re-emitted by the analyte adsorbed on such structures.

In some implementations, the SEL structures are formed from materials and/or are dimensioned so as to bend or flex towards and/or away from one another in response to an applied electric field. In some implementations, the SEL structures are movable and self-actuating such that the structures bend or flex towards one another in response to micro-capillary forces so as to self-organize, wherein such bending facilitates close spacing between the structures for greater scattered radiation or emitted luminescence intensity.

In another implementation, the SEL structures include SEL particles. Examples of SEL particles include, but are not limited to, electrodes in electrolytic cells and metal colloid solutions.

Figure 2:
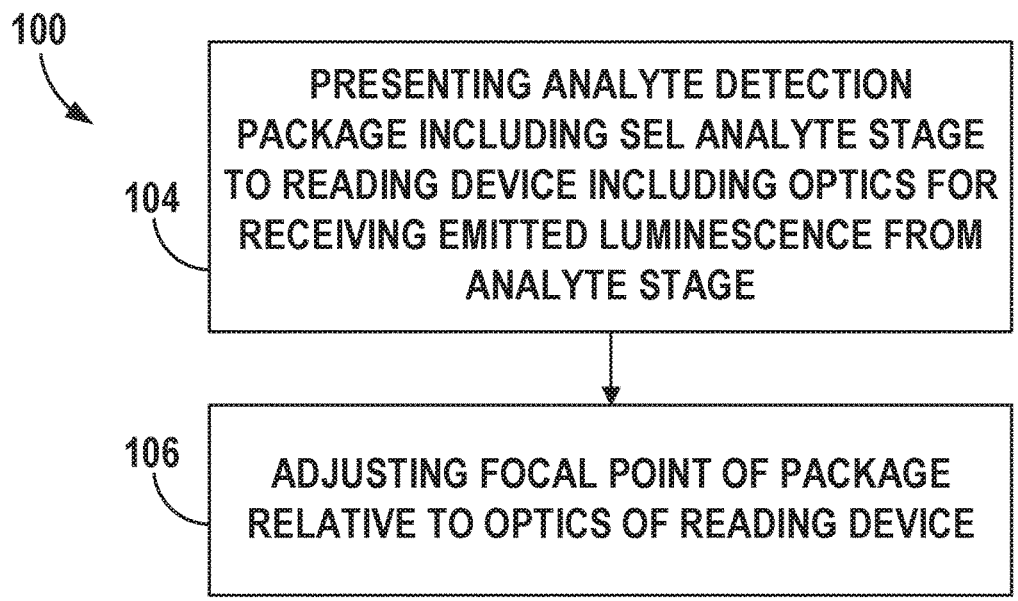
FIG. 2 is a flow diagram of an example method of focusing an example analyte detection package.

FIG. 2 is a flow diagram outlining an example method 100 of focusing an analyte detection package, such as package 20. As indicated by block 104, an analyte detection package is presented to a reading device, such as package 20 presented to reading device 28. The package includes a surface-enhanced luminescence (SEL) analyte stage, such as surface-enhanced luminescence (SEL) analyte stage 42, and the reading device includes optics, such as optics 32, for receiving scattered radiation or emitted luminescence from the analyte stage. As indicated by block 106, a focal point of the analyte detection package is adjusted relative to the optics of the reading device, such as a focal point of package 20 adjusted relative to optics 32 of reading device 28. In one example, the focal point of the analyte detection package is adjusted relative to the optics of the reading device with a focus mechanism, as described below.

Figure 3:
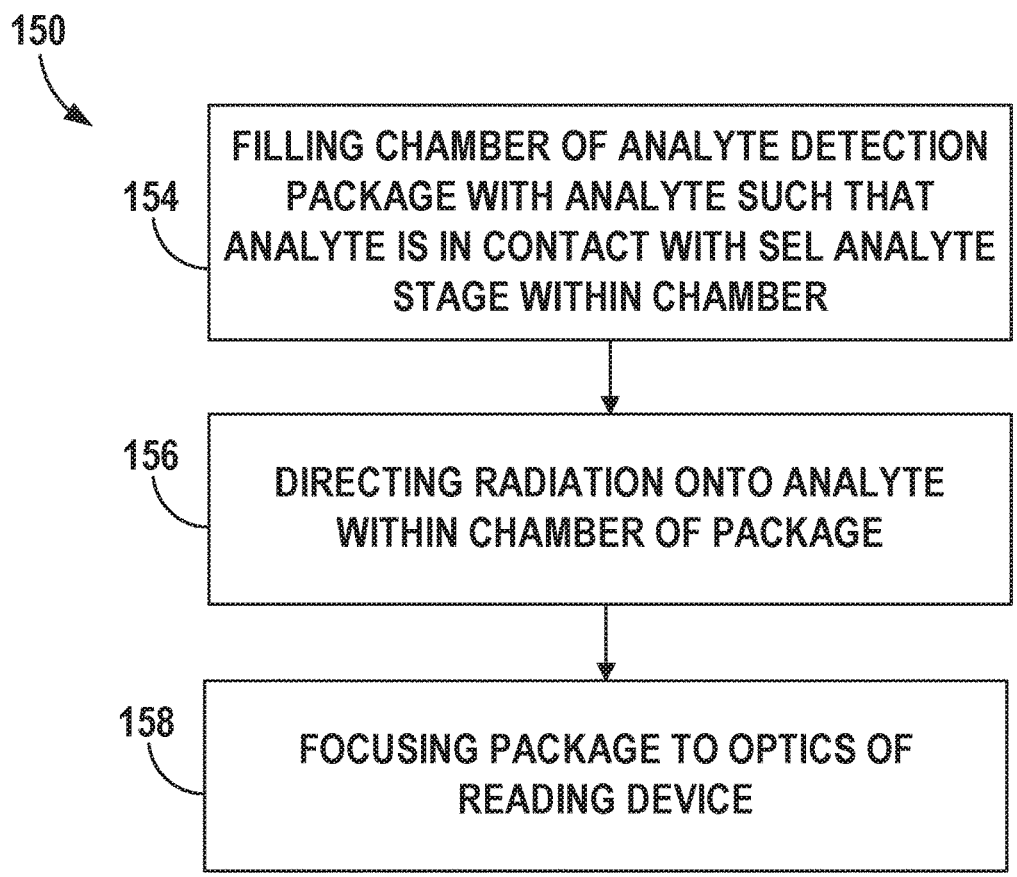
FIG. 3 is a flow diagram of an example method of using an example analyte detection package.

FIG. 3 is a flow diagram outlining an example method 150 of using an analyte detection package when analyzing an analyte, such as package 20 analyzing analyte 24. As indicated by block 154, a chamber of the analyte detection package is filled (partially or fully) with a solution containing the analyte such that the analyte is in contact with an SEL analyte stage within the chamber, such as analyte 24 in contact with analyte stage 42 within chamber 40 of package 20. As indicated by block 156, radiation or light is directed onto the analyte within the chamber of the analyte detection package, such as radiation of radiation source 26 directed onto analyte 24 within chamber 40 of package 20. As indicated by block 158, the analyte detection package is focused to optics of a reading device, such as package 20 focused to optics 32 of reading device 28. In one example, the analyte detection package is focused to the optics of the reading device by a focus mechanism, as described below.

The radiation incident upon the analyte, such as analyte 24, may be scattered by the analyte, or may be absorbed and re-emitted by the analyte. As such, the scattered or re-emitted radiation may be sensed and detected. Signals resulting from the sensed or detected radiation may be analyzed to identify or determine characteristics of the analyte. In one implementation, the analyte, such as analyte 24, is dried or is allowed to dry (the liquid carrier of the analyte is evaporated) within the chamber, such as chamber 40, prior to being impinged with the incident radiation.

Figure 4:
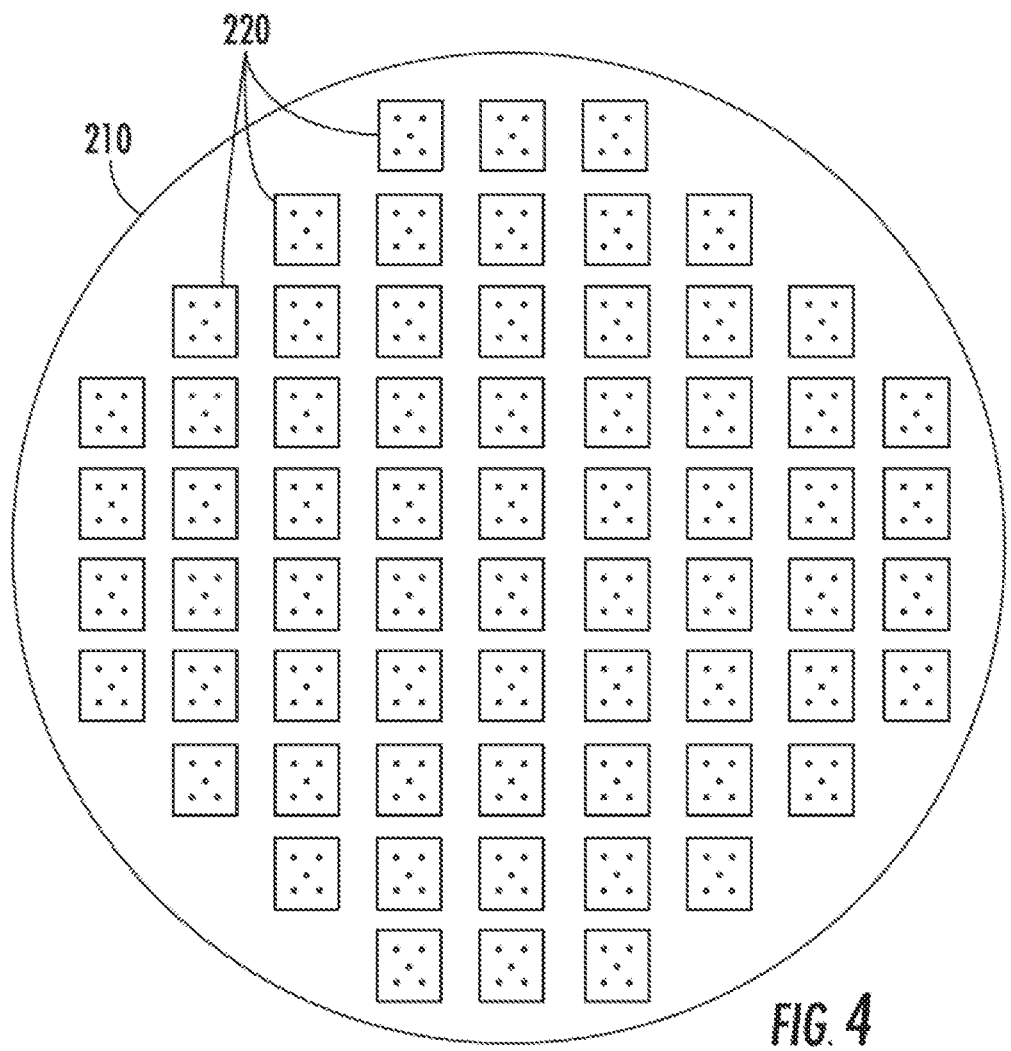
FIG. 4 is an example wafer including an array of example analyte detection packages.
Figure 5:
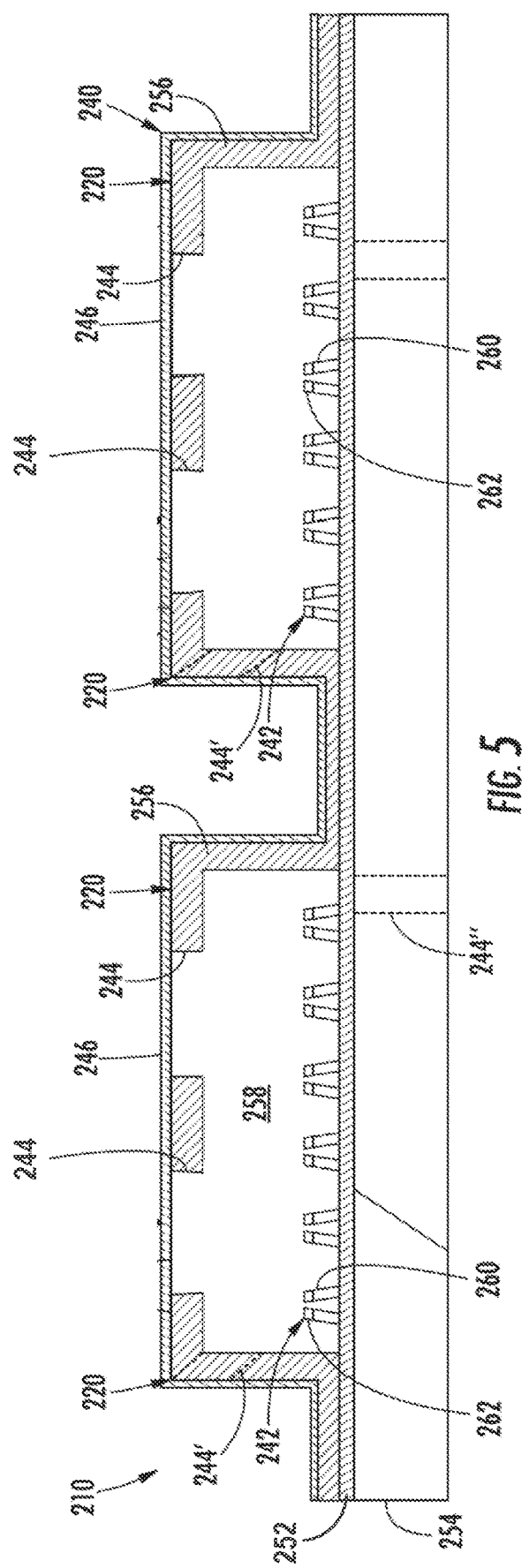
FIG. 5 is a sectional view illustrating example analyte detection packages of the wafer of FIG. 4.

FIGS. 4 and 5 illustrate multiple analyte detection packages 220, as example implementations of analyte detection package 20. As schematically illustrated in the example of FIG. 4, packages 220 may be formed using semiconductor integrated circuit fabrication techniques as part of a wafer 210. The individual packages 220, formed as part of the wafer 210, are then subsequently separated into individual packages or individual sets of packages.

FIG. 5 is a sectional view schematically illustrating two example packages 220 formed as part of wafer 210. As illustrated in FIG. 5, each package 220 includes a chamber 240, a surface-enhanced luminescence analyte stage 242, a fill opening 244, and a seal 246. Similar to chamber 40, chamber 240 contains stage 242 and comprises a defined volume for receiving and containing analyte 24 (FIG. 1). In the example illustrated, chamber 240 is formed or defined by or between a base or substrate 254 and an enclosure or housing 256. Substrate 254 serves as a platform upon which stage 242 is formed, and may be made from any suitable material such as silicon, glass, plastic, paper, polydimethylsiloxane, a transparent material, rubber and/or a membrane, for example.

In one implementation, stage 242 is formed on a layer 252, as supported by substrate 254. Layer 252 comprises a thin-film layer or a layer of a thin-film structure on substrate 254. In one implementation, layer 252 comprises an inter layer dielectric, and may be formed of silicon dioxide (e.g., tetraethoxysilane (TEOS)), silicon nitride, silicon carbide, hafnium oxide or other suitable material or combination of such materials. In other implementations, layer 252 may be a thin-film metal, for example, Au, Ta or other suitable material.

In one implementation, substrate 254 supports housing 256 such that housing 256 extends from substrate 254. In the example illustrated, portions of layer 252 are positioned between substrate 254 and housing 256. In other implementations, housing 256 may contact and directly extend from substrate 254.

Housing 256 cooperates with substrate 254 to form and define an interior 258 of chamber 240. Housing 256 protects stage 242 from exposure to the environment and may reduce or prevent oxidation of surfaces of stage 242 prior to use. Additionally, housing 256 may reduce or prevent unintentional or premature exposure of stage 242 to extraneous substances or an analyte that stage 242 is intended to detect. Although housing 256 and substrate 254 are illustrated as forming a rectangular shaped interior 258, interior 258 may have other shapes in other implementations.

In one implementation, housing 256 comprises an orifice plate and includes walls that are formed by selectively plating a mandrel with a layer or layers of metal and subsequently removing the mandrel to form the housing with apertures. In one implementation, housing 256 has a metal surface such as nickel, gold, platinum or rhodium, for example. In one implementation, the walls of housing 256 are formed entirely from such a metal. In other implementations, housing 256 may be formed from non-metallic materials using processes other than plating.

Stage 242 comprises a surface-enhanced luminescence (SEL) analyte stage within chamber 240, and includes structures 260 that interact with the deposited analyte so as to enhance the intensity of the radiation scattered or re-emitted by the analyte. Such structures enhance the amount of radiation or the number of photons that are scattered or re-emitted by the analyte upon being impinged by radiation from a radiation source.

In the example illustrated, structures 260 comprise columnar structures, such as pillars, needles, wires or fingers. In the example illustrated, each of the structures 260 include a metal cap or head 262 upon which analyte may be deposited. In some implementations, structures 260 are formed from materials and/or are dimensioned so as to bend or flex towards and/or away from one another in response to an applied electric field or in response to micro-capillary forces so as to self-organize, wherein such bending facilitates close spacing between the structures for greater scattered radiation or emitted luminescence intensity. In one implementation, structures 260 have a nanometer scale to facilitate nano-enhanced Raman spectroscopy (NERS). Such nano-scale NERS structures may increase, for example, by a factor as high as $10^{16}$, the intensity of radiation scattered or re-emitted by the analyte absorbed on such structures.

In other implementations, stage 242 comprises other SEL structures such as enhanced fluorescence spectroscopy structures or enhanced luminescence spectroscopy structures. In other implementations, stage 242 comprises particles, such as nanoparticles, that interact with the deposited analyte to enhance the intensity of the radiation scattered or re-emitted by the analyte. Examples of such particles include electrodes in electrolytic cells or metal colloid solutions.

Fill opening 244 comprises a passage extending from the exterior of package 220 to interior 258 of chamber 240. In one implementation, fill opening 244 is sized and located to facilitate filling of interior 258 with the analyte to be tested. In the example illustrated, fill opening 244 extends through housing 256. In other implementations, and as indicated by broken lines, package 220 may additionally or otherwise include other fill openings such as fill opening 244' extending through a side of housing 256 or fill opening 244" extending through substrate 254.

Seal 246 comprises a panel or layer of material coupled or secured to package 220 across or over fill opening 244 so as to cover or close fill opening 244. In one implementation, seal 246 provides a hermetic seal to inhibit contamination of interior 258. For example, seal 246 inhibits oxidation of the metal surfaces within interior 258 prior to use of package 220. Seal 246 further indicates previous use of package 220. Seal 246 may be formed from a polymer tape, plastic, transparent material, plastic sheeting, foil material, foil sheeting, film, membrane, wax or polydimethylsiloxane, for example.

When analyte is to be deposited within interior 258, seal 246 may be altered to provide access through fill opening 244. In one implementation, seal 246 is releasably or removably adhered to housing 256, for example, by pressure sensitive adhesive that allows seal 246 to be peeled away from fill opening 244. In another implementation, seal 246 is formed from a material and/or is dimensioned so as to be punctured through fill opening 244 and/or torn away from fill opening 244. In other implementations, seal 246 comprises a septum that allows insertion of a needle through fill opening 244, wherein the septum resiliently closes upon withdrawal of the needle. In other implementations, seal 246 is provided by a lid, top, door, hatch or cap that temporarily seals or closes fill opening 244. In some implementations, seal 246 is omitted.

Figure 6:
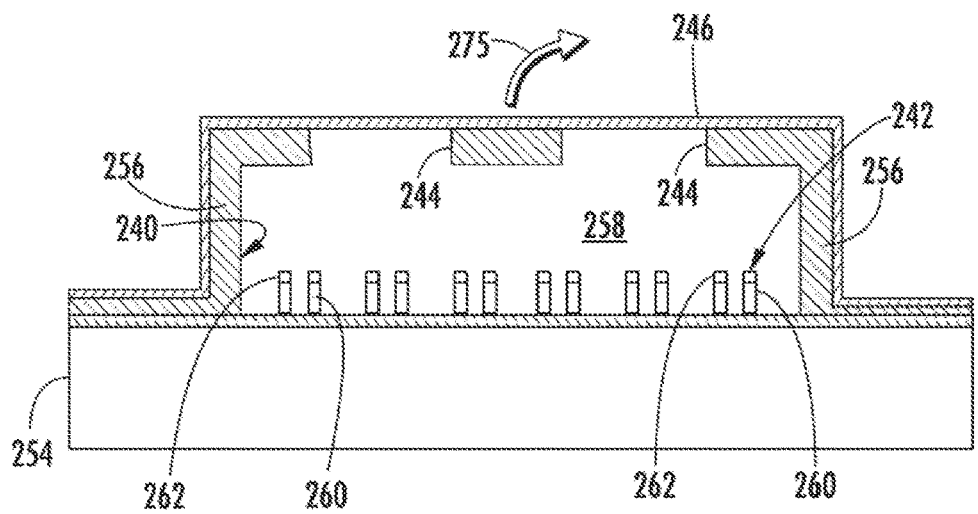
FIGS. 6, 7, and 8 are schematic sectional views illustrating an example method of using an example analyte detection package of FIG. 5.
Figure 7:
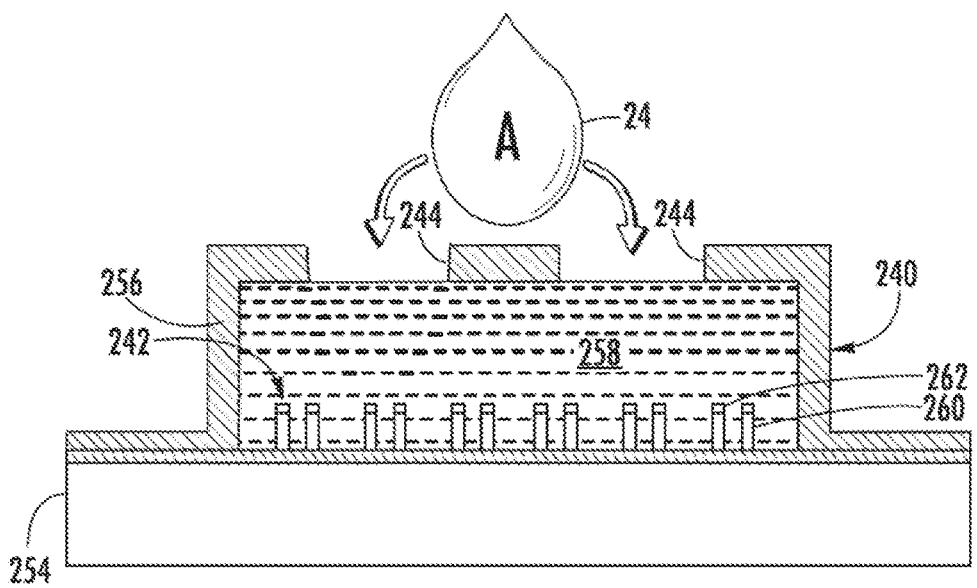
Figure 8:
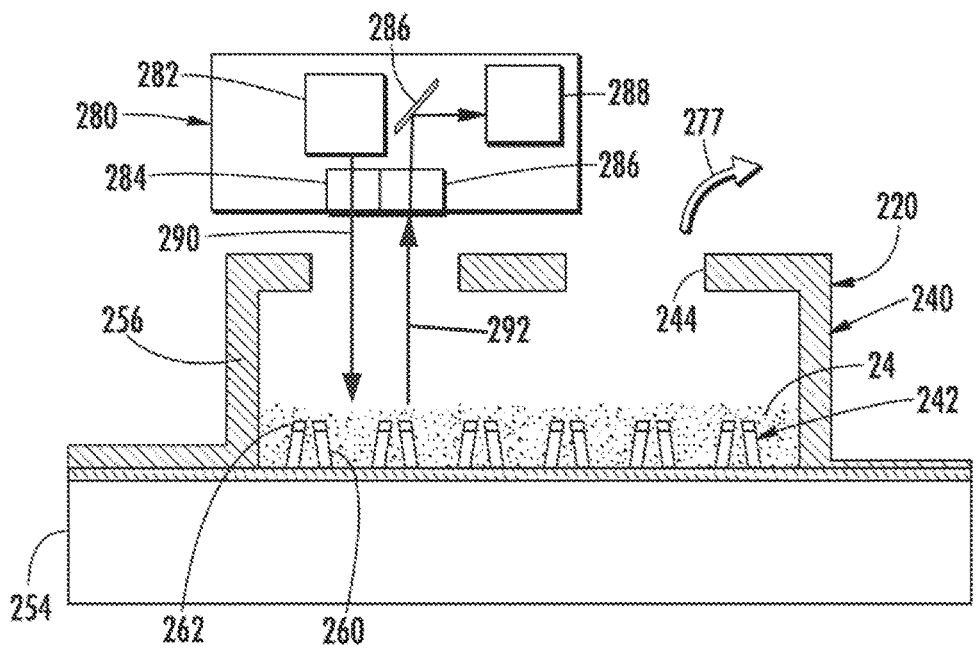

FIGS. 6, 7, and 8 illustrate one example of use of package 220. As illustrated in the example of FIG. 6, seal 246 is peeled away from housing 256, as indicated by arrow 275, and as illustrated in the example of FIG. 7, analyte 24 is deposited into interior 258 through fill opening(s) 244.

As illustrated in FIG. 8, analyte 24 is dried, or allowed to dry or evaporate, as indicated by arrow 277. As further illustrated in FIG. 8, package 220 is presented to a reading device or reader 280 which, in one implementation, comprises a radiation emitter 282, focusing optics 284, receiving optics 286, and a detector 288. Radiation emitter 282 emits photons 290 which are directed by optics 284 onto stage 242 and analyte 24. The directed photons 290 are scattered or re-emitted by analyte 24, wherein the intensity of the scattered or re-emitted photons or radiation is enhanced by stage 242. The scattered or re-emitted photons 292 return to reader 280, where optics 286, in the form of a lens and/or mirror arrangement, direct the scattered or re-emitted photons 292 to detector 288 which outputs signals based upon the detected photons. In one implementation, a processor, following instructions in a non-transitory computer-readable medium, receives the signals and analyzes the signals to identify or determine characteristics of analyte 24.

Figure 9:
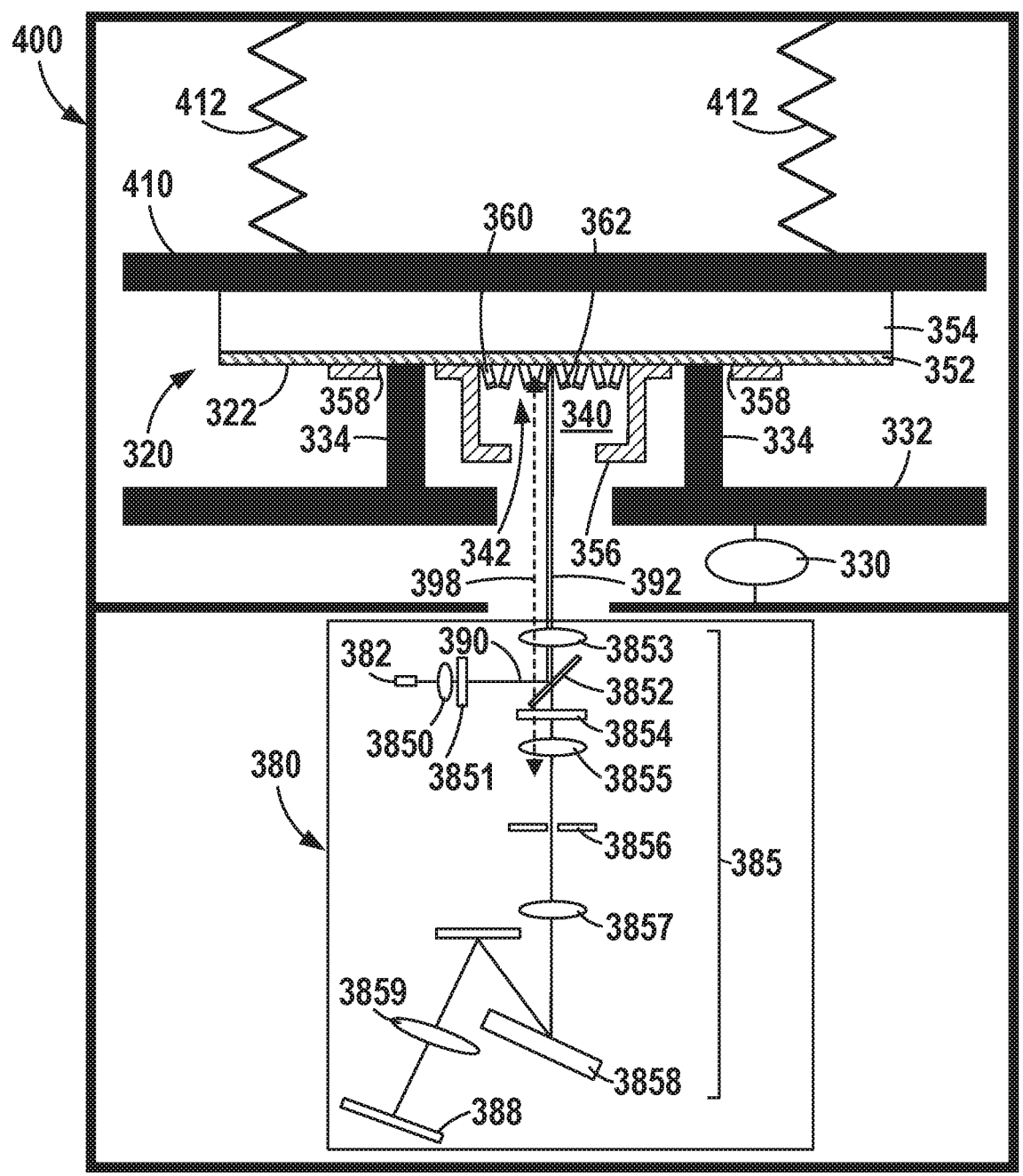
FIGS. 9 and 10 are schematic views illustrating an example of focal adjustment for an analyte detection package.
Figure 10:
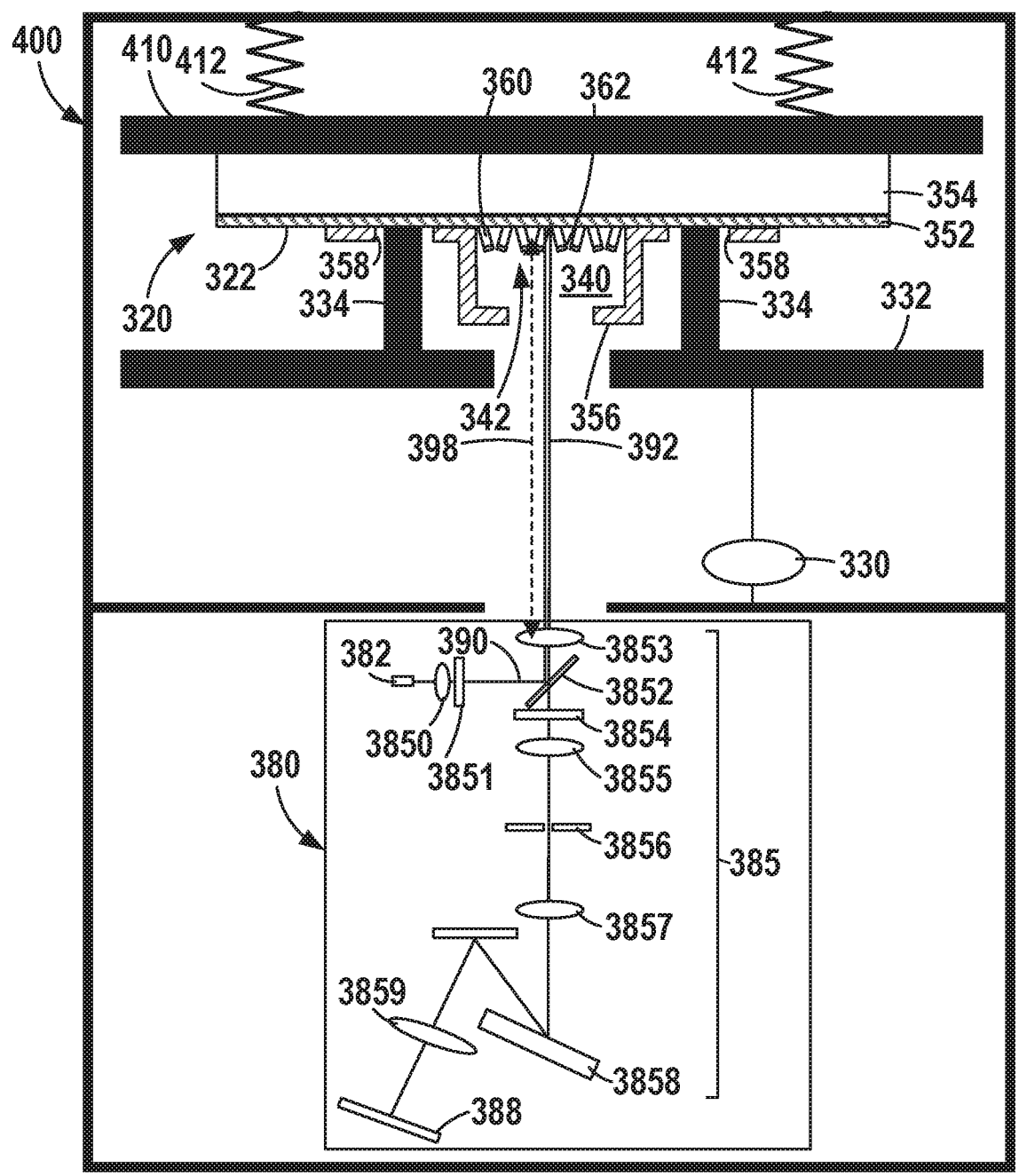

FIGS. 9 and 10 illustrate an example of focal adjustment or focal registration for an analyte detection package 320. Package 320, as an example implementation of package 220 and package 20, includes a chamber 340 and a surface-enhanced luminescence (SEL) analyte stage 342.

Similar to chamber 240 and chamber 40, chamber 340 contains analyte stage 342 and comprises an enclosure forming a defined volume for receiving and containing analyte 24 (FIG. 1). In one implementation, chamber 340 is formed or defined by or between a base or substrate 354 and an enclosure or housing 356.

Similar to stage 242, stage 342 is formed on a layer 352, as supported by substrate 354. Layer 352 comprises a thin-film layer or a layer of a thin-film structure on substrate 354. In one implementation, layer 352 comprises an inter layer dielectric, and may be formed of silicon dioxide (e.g., tetraethoxysilane (TEOS)), silicon nitride, silicon carbide, hafnium oxide or other suitable material or combination of such materials. In other implementations, layer 352 may be a thin-film metal, for example, Au, Ta or other suitable material.

Similar to stage 242 and stage 42, stage 342 includes SEL structures 360 that interact with the deposited analyte to enhance the intensity of the radiation scattered or re-emitted by the analyte. In the example illustrated, structures 360 include columnar structures, such as pillars, needles, wires or fingers. In the example illustrated, each of the structures 360 include a metal cap or head 362 upon which analyte may be deposited.

In the example illustrated in FIGS. 9 and 10, analyte detection package 320 is presented to a reading device 380. Reading device 380, as an example of reading device 280 and reading device 28, includes a light source or radiation emitter 382, optics 385, and a sensor or detector 388, in one implementation. An example of reading device 380 includes a Raman spectrometer.

In one example, radiation emitter 382 includes a laser diode, and optics 385 include collimating lens 3850, laser cleanup filter 3851, dichroic mirror 3852, objective lens 3853, laser blocking filter 3854, focusing lens 3855, slit 3856, collimating lens 3857, grating 3858, and focusing lens 3859.

In the illustrated example, radiation emitter 382 emits photons, as indicated by 390, which are directed by optics 385 onto stage 342 and the analyte. The directed photons are scattered or re-emitted by stage 342 and the analyte, such that the scattering or re-emitting of photons is enhanced by the SEL structures or particles. The scattered or re-emitted photons, as indicated by 392, are returned by optics 385 to sensor or detector 388, and sensor or detector 388 outputs signals based upon the detected photons, such that the signals may be analyzed to identify or determine characteristics of the analyte.

In the example illustrated in FIGS. 9 and 10, a focus mechanism 330 is provided to adjust a focus of analyte detection package 320. Focus mechanism 330 comprises a focus control mechanism or focus adjusting mechanism which provides for movement or adjustment of a focal point of package 320 relative to reading device 380, including, more specifically, movement or adjustment of a focal length between analyte stage 342 of package 320 and optics 385 of reading device 380.

For example, as schematically illustrated in FIG. 9, focal length 398 extends beyond a focal plane of optics 385 of reading device 380 such that analyte detection package 320 is "out-of-focus". However, as schematically illustrated in FIG. 10, with movement by or adjustment of focus mechanism 330, focal length 398 is aligned with a focal plane of optics 385 of reading device 380 such that analyte detection package 320 is "in-focus".

Focus mechanism 330 includes any mechanism, element, component, part, structure, feature, system, assembly, arrangement or combination thereof, that establishes, results in or produces movement, adjustment, positioning or repositioning of analyte detection package 320. Focus mechanism 330 may be manual or automatic. Focus mechanism 330 may be mechanical or electromechanical. Example implementations of focus mechanism 330 may include a screw drive, lead screw, worm gear, rack gear, pinion gear, slider, motor, encoder or combination thereof.

In one implementation, focus mechanism 330 is connected to or interacts with a registration plate 332 to move or adjust a position of analyte detection package 320. As such, focus mechanism 330, with registration plate 332, helps to register, align or position package 320 relative to reading device 380. In one example, registration plate 332 includes registration pins 334 which contact package 320. More specifically, in one implementation, registration pins 334 directly contact a surface 322 of package 320 from which SEL structures 360 extend. As such, reading device 380 may be registered to the same surface from which SEL structures 360 extend.

In the example illustrated, stage 342 is formed on and SEL structures 360 extend from layer 352. As such, surface 322 is formed by layer 352. Thus, in one implementation, registration pins 334 extend through holes or openings 358 in housing 356, as formed on or supported by layer 352, such that registration pins 334 extend through housing 356 and directly contact layer 352.

In one implementation, reading device 380 is supported by, supported in, secured to, positioned in or positioned relative to an enclosure 400, and analyte detection package 320 is supported by, supported in, secured to or positioned relative to enclosure 400 for sensing by reading device 380. As such, focus mechanism 330 is supported by, supported in, secured to, positioned in or positioned relative to enclosure 400 to provide movement or adjustment of analyte detection package 320 relative to reading device 380 and enclosure 400.

In one implementation, analyte detection package 320 is supported or positioned in enclosure 400 by a backing plate 410. In one example, backing plate 410 is biased toward registration plate 332 such that package 320 is biased toward registration plate 332 when supported or positioned in enclosure 400. In one implementation, backing plate 410 is biased by springs 412. As such, analyte detection package 320 is secured, positioned or held between backing plate 410 and registration plate 332, including registration pins 334, as focus mechanism 330 is used to focus analyte detection package 320 relative to reading device 380.

In one implementation, with focus of analyte detection package 320 established, by focus mechanism 330, package 320 may be removed and another package 320 may be inserted, while a position of registration plate 332 is maintained. Thus, focus of the other package 320 may be established based on the prior, maintained position of registration plate 332.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

The invention claimed is:

1. An analyte detection system, comprising:
   an analyte detection package to be presented to a reading device, the analyte detection package including a surface-enhanced luminescence analyte stage having a surface and surface-enhanced luminescence structures extended from the surface, the reading device including optics to receive emitted luminescence from the analyte stage;
   a registration plate to contact the surface of the analyte stage; and
   a focus mechanism to move the registration plate to adjust a focal point of the analyte detection package relative to the optics of the reading device.

2. The system of claim 1, wherein the focus mechanism is registered to the surface of the analyte stage.

3. The system of claim 1, wherein the surface-enhanced luminescence structures are within a chamber of the analyte detection package, wherein the surface of the analyte stage extends externally of the chamber, and wherein the registration plate includes registration pins to contact the surface of the analyte stage externally of the chamber.

4. The system of claim 1, wherein the surface-enhanced luminescence structures comprise surface-enhanced Raman spectroscopy structures.

5. The system of claim 1, wherein the analyte detection package is biased toward the reading device.

6. The system of claim 1, further comprising:
   a backing plate to support the analyte detection package, the analyte detection package to be positioned between the backing plate and the registration plate.

7. The system of claim 6, wherein the backing plate is biased toward the registration plate.

8. The system of claim 1, wherein, with a position of the registration plate maintained, the analyte detection package to be removed from presentation to the reading device and another analyte detection package to be presented to the reading device.

9. An analyte detection system, comprising:
   a surface-enhanced luminescence analyte stage having a surface and surface-enhanced luminescence structures extended from the surface;
   optics to receive emitted luminescence from the analyte stage; and
   a focus mechanism to adjust a focal length between the analyte stage and the optics, the focus mechanism including a registration plate having registration pins in contact with the surface of the analyte stage.

10. The system of claim 9, wherein the focus mechanism is registered to the surface of the analyte stage.

11. The system of claim 9, wherein the analyte stage is biased toward the optics.

12. The system of claim 9, wherein the analyte stage is formed on a layer supported by a substrate, wherein the surface of the analyte stage is formed by the layer.

13. The system of claim 12, further comprising:
   a backing plate to support the substrate, wherein the backing plate is biased toward the registration plate.

14. A method of focusing an analyte detection package, comprising:
   presenting an analyte detection package including a surface-enhanced luminescence analyte stage to a reading device including optics for receiving emitted luminescence from the analyte stage, the analyte stage including surface-enhanced luminescence structures;
   contacting, with a registration plate of a focus mechanism, a surface of the analyte stage from which the surface-enhanced luminescence structures extend; and
   adjusting a focal point of the analyte detection package relative to the optics of the reading device, including moving, via the registration plate, the analyte detection package with the focus mechanism.

15. The method of claim 14, wherein presenting the analyte detection package includes registering the focus mechanism to the surface of the analyte stage.

16. The method of claim 14, wherein the surface-enhanced luminescence structures include surface-enhanced Raman spectroscopy structures.

17. The method of claim 14, wherein presenting the analyte detection package includes biasing the analyte detection package toward the reading device.

18. The method of claim 14, wherein presenting the analyte detection package includes supporting the analyte detection package with a backing plate, including positioning the analyte detection package between the backing plate and the registration plate.

19. The method of claim 18, wherein supporting the analyte detection package with the backing plate includes biasing the backing plate toward the registration plate.

20. The method of claim 14, further comprising:
   with maintaining a position of the registration plate, removing the analyte detection package from presentation to the reading device and presenting another analyte detection package to the reading device.

* * * * *